US00RE39543E

(19) United States
(12) Reissued Patent
Emerson et al.

(10) Patent Number: US RE39,543 E
(45) **Date of Reissued Patent: *Apr. 3, 2007**

(54) USE OF AROMATIC ALDEHYDES AS INSECTICIDES AND FOR KILLING ARACHNIDS

(75) Inventors: Ralph W. Emerson, Davis, CA (US); Bradford G. Crandall, Jr., Davis, CA (US)

(73) Assignee: ProGuard, Inc., Suisun, CA (US)

( * ) Notice: This patent is subject to a terminal disclaimer.

(21) Appl. No.: 08/977,644

(22) Filed: Nov. 24, 1997

Related U.S. Patent Documents

Reissue of:
(64) Patent No.: 5,536,501
Issued: Jul. 16, 1996
Appl. No.: 08/366,974
Filed: Dec. 30, 1994

(51) Int. Cl.
*A01N 25/02* (2006.01)
*A01N 25/32* (2006.01)
*A01N 35/02* (2006.01)

(52) U.S. Cl. ..... 424/405; 424/70.1; 424/84; 424/401; 424/406; 424/407; 424/409; 424/413; 510/278; 514/701

(58) Field of Classification Search ..... 424/403, 424/405–407, 909–911, 414, 417, 418, 421; 514/701
See application file for complete search history.

(56) References Cited

U.S. PATENT DOCUMENTS

| | | | | | |
|---|---|---|---|---|---|
| 52,345 | A | * | 1/1866 | Turney | 424/195.1 |
| 74,940 | A | * | 2/1868 | Rambaut | 424/195.1 |
| 75,161 | A | * | 3/1868 | Heisler | 424/195.1 |
| 450,370 | A | * | 4/1891 | Lintz | 424/195.1 |
| 2,465,854 | A | * | 3/1949 | Dorman et al. | |
| 3,236,869 | A | * | 2/1966 | Thompson | |
| 4,193,984 | A | * | 3/1980 | Kydonieus | |
| 4,402,950 | A | * | 9/1983 | Wolf et al. | |
| 4,477,361 | A | * | 10/1984 | Sperti et al. | |
| 4,808,574 | A | * | 2/1989 | Brekhman et al. | 514/23 |
| 4,833,158 | A | * | 5/1989 | Twydell et al. | 514/616 |
| 4,861,514 | A | * | 8/1989 | Hutchings | 252/187.21 |
| 4,978,686 | A | * | 12/1990 | Sotome | |
| 510,625 | A | * | 9/1992 | Howell et al. | 426/422 |
| 5,149,715 | A | * | 9/1992 | Armstrong et al. | |
| 5,166,317 | A | * | 11/1992 | Wallace et al. | |
| 5,202,247 | A | * | 4/1993 | Kilburn | |
| 5,306,707 | A | * | 4/1994 | Burrell et al. | 512/2 |
| 5,340,731 | A | * | 8/1994 | Kilburn et al. | |
| 5,691,383 | A | * | 11/1997 | Thoms et al. | 514/594 |

FOREIGN PATENT DOCUMENTS

| | | | |
|---|---|---|---|
| FR | 2529755 | | 1/1984 |
| GB | 504125 | | 5/1939 |
| JP | 57120501 | | 7/1982 |
| JP | 59222402 | | 12/1984 |
| JP | 63255203 | | 10/1988 |
| JP | 64-016706 | * | 1/1989 |
| JP | 1261303 | | 10/1989 |
| JP | 3-81203 | * | 4/1991 |
| JP | 3081202 | | 4/1991 |
| JP | 3268901 | * | 11/1991 |
| JP | 4149103 | | 5/1992 |
| JP | 4176460 | * | 6/1992 |
| JP | 50024436 | | 2/1993 |
| JP | 5117125 | | 5/1993 |
| JP | 5139924 | | 6/1993 |
| JP | 6183925 | | 7/1994 |
| WO | WO94/24158 | * | 10/1994 |
| WO | WO94/27434 | | 12/1994 |

OTHER PUBLICATIONS

Arctandef: Perfumed Flavor Chemical #702.*
Bowles & Miller, *J.Food Protection* (1993) 56:788–794.
Frear, *Chemistry of Insecticides and Fungicides* (1942) 13:184–191.
King, *Agriculture Handbook*, (1954) 69:1–397(relevant pages attached).
Lampman & Metcalf, *Environ. Entomol.* (1988) 17: 644–648.
Lampman & Metcalf, *J.Environ. Entmol.* (1987) 80:1137–1142.
Lewis et al. (1990) 19:8–14.
Matsumoto Microbiology Laboratory, *Antimicrobial Test of Avian–M* (1982) 57–07 full cite not available.
Metcalf and Metcalf, "Insect Ecology and Control" in *Plant Kairomones*, Chapman and Hall (1992), pp. 8, 83, 84, 95, 96 and 157.
Metcalf and Metcalf, "Destructive and Useful Insects: Their Habits and Control" in *Insect Control 5th* Edition, McGraw–Hill, Inc. (1993), pp. 7.58–7.60.
Metcalf and Lampman, *J.Econ. Entmol.* (1989) 82:1620–1625.
Metcalf and Lampman, *Experientia* (1989) 45:240–247.
Metcalf and Lampman, *Proc. Natl. Acad. Sci. USA* (1991) 88 1869–1872.
Yuan et al., *Fundamental & Applied Toxicol.* (1993) 20:83–87.*
Casey & Dobb, *Enzyme Microb. Technol,* (1992) 14:739–747.*

* cited by examiner

*Primary Examiner*—Neil S. Levy
(74) *Attorney, Agent, or Firm*—Dorsey & Whitney LLP

(57) ABSTRACT

Methods and compositions based upon natural flavonoid aldehydes are provided, which find use as pesticides. The pesticides are formulated in a variety of ways, including dusts, sprays, shampoos and soaps, and can be bound to a solid support or provided as bait or directly impregnated into organic matter infested by or susceptible to infestation by a target pest.

14 Claims, No Drawings

USE OF AROMATIC ALDEHYDES AS INSECTICIDES AND FOR KILLING ARACHNIDS

Matter enclosed in heavy brackets [ ] appears in the original patent but forms no part of this reissue specification; matter printed in italics indicates the additions made by reissue.

CROSS-REFERENCE TO RELATED APPLICATIONS

This application is related to applications Ser. No. 08/366,973, filed Dec. 30, 1994, and Ser. No. 08/367,082 filed Dec. 30, 1994 which applications are hereby incorporated by reference.

INTRODUCTION

1. Technical Field

The present invention is related to the biocontrol of insects and arachnids using flavenoid aldehydes.

2. Background

Organic matter, including decaying organic matter, is colonized by a variety of organisms, many of which are dependent upon a particular organic material as a source of nutrients. The colonizing organisms include a variety of insects and arachnids, some of which spread disease and/or damage the material which they colonize. The insects and arachnids which colonize particular organic materials include those species which are symbiotic with bacteria, such as cockroaches, fleas, termites and spider mites; the host organism cannot survive without the symbionts.

A variety of compositions are used for controlling insect and arachnid pests. However, the wide-spread use of pesticides has resulted in the development and evolution of resistant pests, as well as growing environmental and health care concerns. A highly visible ecological-environmental activist community and public regulatory agencies have resulted in fewer and fewer pesticide registrations and, consequently, less related research and development. It therefore is of interest to identify and/or develop, "biorational" formulations which have lower animal and environmental toxicities yet are effective in controlling insect and arachnid pests.

RELEVANT LITERATURE

A method of protecting crops from attack of pests including insects using a composition comprising cinnamic aldehydes and requiring an antioxidant is disclosed in U.S. Pat. No. 4,978,686. Protection of crops against insect pests by applying an aqueous composition containing a cinnamaldehyde is disclosed in French patent application 2529755. U.S. Pat. No. 2,465,854 describes an insecticidal composition containing a cinnamic aldehyde derivative.

U.S. Pat. No. 4,402,950 describes the deactivation of viruses inside living human and animal organisms by application of a terpene obtainable from aromatic plants by steam application. The terpenes cited are: black pepper oil, cinnamon flour oil, cardamon oil, linallyl acetate, cinnamic aldehydes, safrol, caryon and cis/trans citrao. Antifungal-antibacterial detergents containing cinnamic compounds are reported in U.S. Pat. No. 4,477,361.

SUMMARY OF THE INVENTION

The present invention provides a method for controlling insect and arachnid pest populations through nutritional mediation using flavonoid aldehydes. The method includes the step of contacting a target pest with an amount of a flavonoid aldehyde sufficient to control growth of the target pest. The aldehydes can be provided in a variety of formulations, including as a component of a trap which optionally contains a chemoattractant for the target pest. The growth modulating product has a formula shown in (1) below.

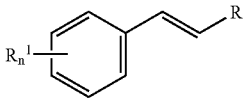

(1)

wherein R represents —$CH_2OH$, CHO or H; n is an integer from 0 to 3; and each $R^1$ independently represents OH, —H, or an organic substituent containing from 0 to 10 carbon atoms and from 0 to 5 heteroatoms, wherein the total number of carbon and heteroatoms in all $R^1$ substituents of said compound is no more than 15. These compounds include natural compounds such as cinnamaldehyde, coniferyl aldehydes, and closely related compounds. The invention finds use in controlling pest populations in areas of infestation, or areas susceptible to infestation.

BRIEF DESCRIPTION OF SPECIFIC EMBODIMENTS

Methods and compositions are provided for obtaining and/or maintaining an area substantially free of pests such as insects and arachnids using flavonoid aldehydes to biocontrol the area. By "biocontrol" is intended control of pests via direct pesticidal activity on a target pest or by indirect pesticidal activity by antibacterial action on symbiont bacteria resident in the target pest.

A target pest colonizing an area is contacted with a natural product. By "colonizing" is intended association of a pest with an area which provides access to organic matter which serves as a source of nutrients for the pest, typically essential nutrients such as amino acids, particularly methionine. By "natural product" is intended an organic compound of natural origin that is unique to one organism, or common to a small number of closely related organisms, and includes secondary metabolites provided by the organic matter. The natural products can be isolated from a natural source, be wholly or partially synthetic, or be produced by recombinant techniques. The amount of natural product that is provided, either applied to organic matter colonized by the target pest or as bait, will depend upon the degree of infestation of the area and to some extent upon the formulation and the specific compounding used and therefore must be empirically determined for best results.

The compositions and methods of the subject invention offer several advantages over existing compositions and methods, including that they are safe for use around humans, animals and food sources. Additionally, the compositions can be used to impregnate organic matter which serves as a nutrient source for a target pest and/or can be provided bound to a solid support which itself is non-toxic to animals, including humans.

The subject formulation is as shown in formula (1) above. A preferred formulation is shown in formula (2) below.

(2)

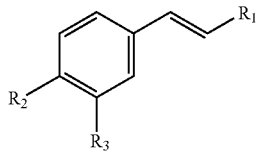

Wherein $R_1$ represents —CHO, $R_2$ represents OH, —H or an organic substituent containing from 1 to 10 carbon atoms, and $R_3$ represents a methoxy group, —H, or an organic substituent containing from 1 to 10 carbon atoms. Of particular interest are flavonoid aldehydes, particularly aromatic aldehydes. Examples of aromatic aldehydes of use in the present invention are cinnamic aldehydes ((3) below)

(3)

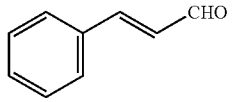

and coniferyl aldehyde ((4) below).

(4)

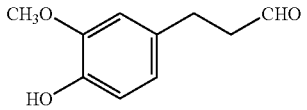

A number of the aromatic and aliphatic aldehydes which may find use in the subject invention, such as benzaldehyde, acetaldehyde, cinnamaldehyde, piperonal, and vanillin are generally regarded as safe (GRAS) synthetic flavoring agents (21 CFR §172.515). The general formula of these compounds is shown above as (1).

The compounds may be used either alone or in combination with other active or inactive substances and may be applied by spraying, pouring, dipping, in the form of concentrated liquids, solutions, suspensions, powders and the like, containing such concentration of the active compound as is more suited for a particular purpose at hand. They may be applied, for example, in the form of dilute solution, in a suitable solvent directly to an area of pest infestation or an area susceptible to infestation or bound to a solid support for application in powder form or in a "trap".

For use as a means of cleansing a surface, such as a carpet, pet bedding, pet fur and the like, although the aldehyde can be formulated alone as an aqueous solution, it also can be prepared as a soap or a detergent. Detergents which can be used include anionic detergents such as those described in U.S. patent application Ser. No. 4,978,686. Additional components such as an aqueous preparation of a salt of a polyprotic acid such as sodium bicarbonate, sodium sulfate, sodium phosphate or sodium biphosphate can be included in the formulation, to increase the pesticidal properties of the formulation. The resulting emulsion is diluted to an appropriate concentration for use, and is additionally provided as a formulation suitable for the intended application, i.e. carpet shampoo, detergent, or animal shampoo or soap including shampoo or soap for human use.

For applications where the formulation is to be used as a trap or as bait for a particular pest, the formulations of the subject invention can be sprayed directly in an area of infestation or they can be bound to a solid support or encapsulated in a time release material. Where a solid carrier is used, materials which can lead to oxidation of the active aldehydes should be avoided. Examples of delivery systems include starch-dextran, and the like. See Yuan et al., Fundamental and Applied Toxicology (1993) 20:83–87 for examples of delivery systems.

In addition to the specific compounds of the formulas (1), (2) and (3), set forth above, derivatives of any of these compounds that produce a compound of the formula identified above upon action of a biological system on the derivative are considered to be equivalent to compounds of the invention. Thus application of precursor compounds to pests which can metabolize the precurors to produce a specific compound identified above would be equivalent to the practice of the present invention. Biological conversion of precursor compounds into flavonoid aldehydes is described in, for example, U.S. patent application Ser. No. 5,149,715 and references cited therein. See also Casey and Dobb Enzyme Microb. Techol. (1992) 14: 739–747.

The method of the present invention is carried out by introducing into a target pest a sufficient amount of a pesticide to impair growth and/or viability of the target pest and thereby decrease the population of that pest in an area. A formulation containing the pesticide is introduced to an area of infestation. For example, the formulation is sprayed on as a wet or dry formulation on the surface of organic material infected with a target pest, or organic material susceptible to infestation with a target pest. Alternately, the formulation can be applied wet or dry to the an area of infestation where it can contact the target pest. In some instances, time-release formulations may find use, particularly for applications to animals, or areas which are subject to reinfestation, such as animal quarters.

The method of introducing of the subject pesticide into the target pest can be by direct ingestion by the target pest from a trap, or by feeding of a target pest on nutrient-providing organic matter treated with the pesticide. In some instances, the pesticide may be absorbed by the pest, particularly where the formulation provides for uptake by the outer tissues of the pest, particularly a larval or other pre-adult form of the pest, such as a detergent formulation.

For some applications, such as infestations of cockroaches and termites, it is necessary to deliver the formulation to the location of the pest colony. When used in a solid form or microencapsulated, the dosage used would typically be on the order of 1% to 35% on a w/w basis, the maximum loading to be determined as a function of shell material selected. Analytical chemical techniques are used to determine and optimize rate of release. For qualitative purposes, GC techniques can be used to determine the amount of aldehydes released. The samples of encapsulated (pelletized) product are sampled at different time periods to measure release. Alternatively, volatile gases released from the formulation can also be analysed. For measuring the activity of spray or powder applications the stability of the formulations over time can also be evaluated by the GC methodology using techniques known to those skilled in the art. Methanol or alcohol extractions of the formulations also can be prepared and evaluated by HPLC analysis.

The aldehyde components can be coupled to a solid support, optionally through a linker such as a polysaccharidase binding domain, where the solid support is a polysaccharide such as cellulose, particularly microcrystalline cellulose. The preparation of cellulase binding domains is described in U.S. patent application Ser. Nos. 5,340,731; 5,202,247 and 5,166,317. The aldehydes can be coupled to the binding domains, with or without a cleavable bond, using methods well known to those skilled in the art. These formulations can be used to directly impregnate a surface comprising the appropriate polysaccharide, for example where the surface is a cellulose, such as paper or wood, a cellulase binding domain is used. As an example, the flavenoid aldehyde-cellulase binding domain composition can be used to impregnate wood which is subject to or already infested with termites. In other applications, the aldehyde-cellulase binding domain composition can be found to paper as a trap or to microcrystalline celluose wherein the granules can be transported back to the colony. Optionally, the bait or trap additionally can include a chemoattractant for the target pest, such as putrescine for flies or cadavarine for cockroaches bound to the cellulose support via a cellulase binding domain. Other examples of chemoattractants are well known to those skilled in the art.

In addition to providing bait or traps, infestations of target pests also can be treated using powder or detergent formulations, for example as a carpet shampoo to treat infestations of dust mites and fleas and other susceptible pests. The formulations of the subject invention generally are non-staining and additionally often impart a pleasant odor to the treated surface.

The formulations also can be used as powders, soaps or detergents for treatment of infestations of animals or humans, including infestations with fleas and ticks. In some instances it may be necessary to adjust the treatment formulation so as to reduce any dermatological effects associated with the treatment. Generally, the formulations are safe for ingestion and additionally, typically have positive organoleptic and olefactory characteristics.

The target pests include insects and arachnids, particularly those which colonize organic matter, more particularly organic matter which is an elicitor for the pest. By elicitor is intended that the organic matter provides nutrients required by the pest. Examples of pests and the organic matter or habitat which provides their nutrients are as follows. Muscaro domesfica (L.) and Stomoxys calcitranus (L.), decaying organic matter, particularly matter, which includes putrescine; Aphaniptera (Siphonaptera), blood; Argas (Persicargas) arboreus (Ixodoidea: Argasidae), blood; Dictyoptera: Blattellidae, decaying organic matter; Isoptera: Rhinotermitidae, organic matter, particularly matter containing cellulose. Also of interest are mites, such as spider mites (arthropoda), dust mites, mites which infect honey bees and a variety of other mites. It is a theory of the invention that many of the insects and arachnids which are susceptible to treatment with the subject formulations are those which harbor symbiotic bacteria in their gut. Accordingly, insects and arachnids other than those listed which harbor symbiotic organisms can also be controlled with the subject formulations.

In order to determine the susceptibility of particular pests to the subject compositions, in vitro and in vivo tests such as are described in the Examples can be used. As appropriate, the formulations also need to be evaluated for dermatological effects; it therefore is important where appropriate that at least one evaluation of the toxicity of the formulations be tested on animal hosts for the target pest or on animals which may come in contact with a treated surface so that the dermatological effects can be tested for the dosage of pesticide used. Such dermatological sensitivity tests can be conducted using methods known to those skilled in the art.

The following examples are offered by way of illustration and not by way of limitation.

EXAMPLES

EXAMPLE 1

Protocol for Spider Mite

Activity of cinnamic aldehyde and/or coniferyl aldehydes against two-spotted spider mite, Tetranychus urticae is determined as follows:

Petri Dish Bioassay

Each petri dish (60 mm diameter) is treated with a specific rate of product (e.g. 10–100 ppm) dissolved in water, and allowed to dry. Twenty specimens of each arthropod are put in each dish, (replicate 10 times). The mortality after three hours in contact with a treated petri dish, is compared to that of arthropods in petri dishes treated only with diluent.

Plant Foliar Bioassay

Cotton plants are grown in 7.5 mm pot in potting soil in greenhouse. When plants reach 3 leaf stage, they are infested with 60 of the specified arthropod (6 replications). The mite is allowed to settle and feed. The plant is sprayed to runoff with a formulation containing 100 to 2000 ppm, or 0.1 to 2 g/l concentration of a test formulation. The plant is covered with a tall plastic cage (5 mm tall×10 mm diameter). The mortality after three days of the mites on the plants sprayed with a test formulation is determined and compared with that of mites on plants sprayed only with water.

EXAMPLE 2

Treatment for Flies

In an air conditioned case measuring 1.5 m×1.5 m×1.5 m, 150 flies (Musca domestica (1..) and Stomoxys calcitranus (1..) are released and sprayed with 8 ml of test product. The test product contains 100 to 2000 ppm of cinnamic aldehyde and/or coniferyl aldehyde in an appropriate formulation. After 15 minutes exposure, the number of flies that are unable to fly are noted. All flies are transferred to a holding case with fresh air and allowed to recuperate for 20 hours. The number of dead flies are counted, and the percentage of flies killed with each formulation compared to that of no treatment and treatment with a formulation known to kill files at a level of about 70%.

EXAMPLE 3

Treatment of Fleas

Petri Dish Bioassay (Aphanptera (Siphonaptera)) susceptibility is tested as follows. Petri dishes (60 mm diameter) are treated with a specific dose of product (100 to 2000 ppm) dissolved with water, and allowed to dry. Twenty specimens of the insect and twenty larvae of the insect each are put in separate dishes (replicate 10 times). The mortality of insect and larvae after thirty hours in contact with a treated plate is compared to that of insects and larvae treated only with the diluent, and treatment with a formulation known to kill fleas at a level of about 70%.

EXAMPLE 4

Treatment of Ticks

Petri dishes (80 mm diameter) are treated with a specific rate of product (e.g. 10 to 2000 ppm) dissolved in water and allowed to dry. Twenty five specimens of the arachnid (Argas (Persicargas) arboreus (Ixooldea: Argasidae) are put in each dish, replicate 10 times. The mortality after 30 hours in contact with a treated plate is compared to that of arachnids in petri dishes treated only with the diluent, or with a formulation known to kill tick at a level of about 70%.

EXAMPLE 5

Treatment Of German Cockroaches

Topical application Bioassay

Adult male cockroaches (Dictyoptera,Blattelidae) are used to evaluate insecticidal activity of cinnamic aldehydes and/or coniferyl aldehydes by a topical application method. The topical application is made by an ISCO model M microapplicator. Cockroaches are anesthetized with $CO_2$ then treated with 1 ml formula containing 1 to 2000 ppm of cinnamic aldehyde and/or coniferyl aldehydes by placing a microdroplet of solution on the ventral aspect of the penultimate abdominal segment using a 27-gauge needle on a glass tuberculin syringe. Ten cockroaches are treated with each formula and the experiment replicated three to five times. Treated cockroaches are placed in glass jars (0.95 liter) provisioned with food, water and harborage. The number of dead or moribund cockroaches 24 h after treatment is counted and compared to those untreated (diluent only) or treated with a formulation known to kill approximately 70% of a cockroach population.

EXAMPLE 6

Treatment of Western Subterranean Termites (Isoptera: Rhinotermitidae) Laboratory Bioassay Tray Bioassay Sterilized play sand is treated with aqueous emulsions of each formula and component to provide 500 ppm deposits (wt./wt. sand). 500 g samples of sand are evenly spread ≦1 mm thick over a metal tray (50 by 30 cm) and sprayed with 65 ml of emulsion with an air brush at 1,970 g/cm$^2$ (28 psi) to obtain uniform treatments. Six examples for each formula and component are prepared. The treated sand is dryed in a fume hood for 30 minutes and the insecticidal activity of each formula treated sand is determined by continuously confining termites to treated deposits for 24 h. Ten termites are exposed on 2.5 ml of treated sand in petri dishes (35 by 10 mm) in each of five replicates. Termites and petri dishes are held in a chamber maintained at 93% RH with a saturated sodium sulfate solution. The number of dead or moribund termites after 24 h exposure is determined. Termites are considered dead if unable to right themselves within 5 min. The effectiveness of the test formulation is compared to termites treated with diluent only or with a formulation known to kill termites at a level of about 70%.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now having been fully described, it will be apparent to one of ordinary skill in the art that many changes and modifications can be made thereto without departing from the spirit or scope of the appended claims.

What is claimed is:

1. A method for [controlling an insect or an arachnid population,] *killing a population of pests selected from the group consisting of termites, ants, mites, and fleas,* said method comprising:

contacting said [insect or arachnid] population *of pests* with an effective pest growth modulating amount of [a] *an aqueous* formulation comprising 0.01 g/l to [25 g/l of one or more compounds having a formula

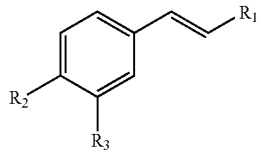

wherein $R_1$ represents —CHO, $R_2$ represents —OH, H or an organic substituent containing from 1 to 10 carbon atoms, and $R_3$ represents a methoxy group, H or an organic substituent containing from 1 to 10 carbon atoms;] *10 g/l of one or more of compounds selected from the group consisting or cinnamic aldehyde and coniferyl aldehyde,* and wherein said formulation does not contain an antioxidant other than an antioxidant according to said [formula.] *compounds.*

[2. The method according to claim 1, wherein said effective insect or arachnid growth modulating amount is 2.5 g/l to 12.5 g/l.]

[3. The method according to claim 1, wherein said one or more compounds are of cinnamic aldehyde or coniferyl aldehyde.]

4. The method according to [claim 3,] *claim 1,* wherein said *aqueous* formulation provides for about 70% or greater kill of said [insect or arachnid] *pest* population.

5. The method according to [claim 1, wherein said formulation is free of antioxidants other than compounds of a formula

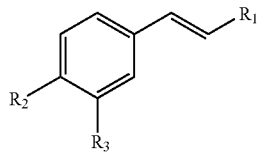

wherein $R_1$ represents —CHO, $R_2$ represents —OH, H or an organic substituent containing from 1 to 10 carbon atoms, and $R_3$ represents a methoxy group, H or an organic substituent containing from 1 to 10 carbon atoms.] *claim 1, wherein said aqueous formulation further comprises a salt of a polyprotic acid.*

[6. The method according to claim 1, wherein said insect or arachnid population is selected from the group consisting of a cockroach, an ant, and a mite.]

7. A composition suitable for use as bait for [an insect or arachnid] *the group of pests consisting of arachnids, flies, cockroaches, and termites* comprising:

one or more compounds [having a formula

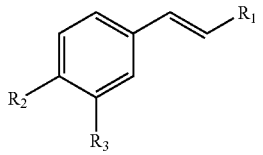

wherein $R_1$ represents —CHO, $R_2$ represents —OH, H or an organic substituent containing from 1 to 10 carbon atoms, and $R_3$ represents a methoxy group, H or an organic substituent containing from 1 to 10 carbon atoms, associated with a solid support.] *selected from the group consisting of cinnamic aldehyde and coniferyl aldehyde, wherein said composition is linked to a solid support, and said composition is free of antioxidants other than said compounds.*

[8. A composition suitable for use as a shampoo or a soap, said composition comprising:

an insect or arachnid growth modulating amount of one or more compound of a formula

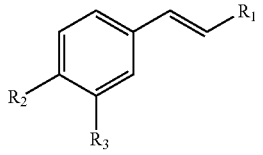

wherein $R_1$ represents —CHO, $R_2$ represents —OH, H or an organic substituent containing from 1 to 10 carbon atoms, in a soap or detergent formulation and $R_3$ represents a methoxy group, H or an organic substituent containing from 1 to 10 carbon atoms, to provide a kill of about 70% or greater of a target insect or arachnid population.]

[9. The composition according to claim 8, wherein said one or more compounds are cinnamic aldehyde or coniferyl aldehyde.]

[10. The composition according to claim 9, wherein said composition is free of antioxidants other than compounds of a formula

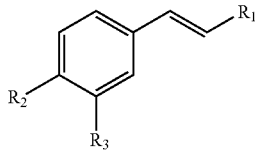

wherein $R_1$ represents —CHO, $R_2$ represents —OH, H or an organic substituent containing from 1 to 10 carbon atoms, and $R_3$ represents a methoxy group, H or an organic substituent containing from 1 to 10 carbon atoms.]

[11. The composition according to claim 10, wherein said composition comprises compounds of cinnamic aldehyde and coniferyl aldehyde.]

12. [A] *The* composition according to claim 7, wherein said solid support comprises cellulose.

13. [A] *The* composition according to claim 12, wherein said [one or more] compound [of the formula

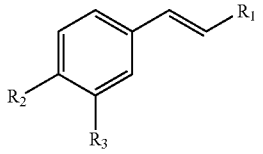

wherein $R_1$ represents —CHO, $R_2$ represents —OH, H or an organic substituent containing from 1 to 10 carbon atoms, and $R_3$ represents a methoxy group, H or an organic substituent containing from 1 to 10 carbon atoms,] is [associated] reversibly linked with said cellulose.

14. [A] *The* composition according to claim 12, wherein said [associated is] *composition is linked to said solid support* via a cellulose binding domain.

[15. A composition according to claim 7, wherein a chemoattractant for said insect or arachnid is associated with said solid support.]

16. The composition according to claim 7, wherein said solid support is enclosed in a housing having means of ingress and egress for said [insect or arachnid] *group of pests*.

*17. The method according to claim 4, wherein said aqueous formulation further comprises a soap or detergent suitable for use as a shampoo or soap for a mammal.*

*18. The method according to claim 4, wherein said aqueous formulation further comprises a powder or detergent suitable for use a carpet shampoo.*

*19. A composition suitable for use as bait for the group of pests consisting of flies, cockroaches, and termites comprising cinnamic aldehyde linked to a solid support.*

*20. A method for killing a population of pests selected from the group consisting of termites, ants, mites, and fleas, said method comprising:*

*contacting said population of pests with an effective pest growth modulating amount of an aqueous formulation comprising 0.01 g/l to 10 g/l of one or more of compounds selected from the group consisting of cinnamic aldehyde and coniferyl aldehyde, and wherein said formulation is linked to a solid support and does not contain an antioxidant other than an antioxidant according to said compounds.*

*21. A method for killing a population of pests selected from the group consisting of termites, ants, mites, and fleas, said method comprising:*

*applying a composition comprising one or more compounds selected from the group consisting of cinnamic aldehyde and coniferyl aldehyde in an area infested with said population of pests, wherein said composition is linked to a solid support and is free of antioxidants other than said compounds.*

*22. A composition suitable for use as bait for the group of pests consisting of arachnids, flies, cockroaches, and termites comprising:*

*one or more compounds selected from the group consisting of cinnamic aldehyde and coniferyl aldehyde, wherein said composition is linked to a solid support, located adjacent to an area of infestation of said pests, and does not contain an antioxidant other than an antioxidant according to said compounds.*

* * * * *